US010751083B2

(12) United States Patent
McGuckin, Jr.

(10) Patent No.: US 10,751,083 B2
(45) Date of Patent: Aug. 25, 2020

(54) ATHERECTOMY DEVICE

(71) Applicant: Rex Medical, L.P., Conshohocken, PA (US)

(72) Inventor: James F. McGuckin, Jr., Radnor, PA (US)

(73) Assignee: Rex Medical L.P., Conshohocken, PA (US)

( * ) Notice: Subject to any disclaimer, the term of this patent is extended or adjusted under 35 U.S.C. 154(b) by 0 days.

(21) Appl. No.: 16/383,602

(22) Filed: Apr. 13, 2019

(65) Prior Publication Data

US 2019/0239921 A1    Aug. 8, 2019

Related U.S. Application Data

(62) Division of application No. 14/616,670, filed on Feb. 7, 2015, now Pat. No. 10,271,869.

(Continued)

(51) Int. Cl.
*A61B 17/3207* (2006.01)
*A61B 17/32* (2006.01)
(Continued)

(52) U.S. Cl.
CPC .............. *A61B 17/320758* (2013.01); *A61B 17/32002* (2013.01); *A61B 17/3207* (2013.01);
(Continued)

(58) Field of Classification Search
CPC .... A61B 17/320758; A61B 17/320016; A61B 17/32002; A61B 17/3207; A61B 2017/320716; A61M 1/0082
See application file for complete search history.

(56) References Cited

U.S. PATENT DOCUMENTS 4,445,509 A   5/1984   Auth
4,883,458 A   11/1989  Shiber
(Continued)

FOREIGN PATENT DOCUMENTS

CN      102670283     9/2012
NL      1034242       8/2008
(Continued)

OTHER PUBLICATIONS

The Extended European Search Report Application No. 15155876.4 dated Jul. 6, 2015.

(Continued)

*Primary Examiner* — Matthew F Desanto
(74) *Attorney, Agent, or Firm* — Neil D. Gershon

(57) ABSTRACT

A surgical apparatus for removing deposits from an interior of a vessel including an outer member and a rotatable shaft having a lumen to receive a guidewire. The lumen has a cross-sectional dimension to enable fluid injection between an inner diameter of the shaft and an outer diameter of the guidewire. A tip is mounted to the shaft for rotation about its longitudinal axis and mounted such that the distal opening of the shaft is axially spaced from a distal internal surface of the tip such that fluid injected through the lumen of the shaft contacts the distal internal surface of the tip and is redirected proximally to direct in a proximal direction deposits removed by the rotational movement of the shaft. The tip includes including a guidewire lumen for receiving a guidewire to enable over the wire insertion of the apparatus.

18 Claims, 12 Drawing Sheets

Related U.S. Application Data

(60) Provisional application No. 61/946,733, filed on Mar. 1, 2014.

(51) Int. Cl.
    *A61B 17/00*             (2006.01)
    *A61M 1/00*             (2006.01)

(52) U.S. Cl.
    CPC ............ *A61B 17/320016* (2013.01); *A61B 2017/00685* (2013.01); *A61B 2017/320716* (2013.01); *A61B 2217/005* (2013.01); *A61B 2217/007* (2013.01); *A61M 1/0082* (2014.02)

(56) References Cited

U.S. PATENT DOCUMENTS

| | | | |
|---|---|---|---|
| 4,957,482 | A | 9/1990 | Shiber |
| 4,979,939 | A | 12/1990 | Shiber |
| 4,990,134 | A | 2/1991 | Auth |
| 5,019,089 | A | 5/1991 | Farr |
| 5,047,040 | A | 9/1991 | Simpson |
| 5,114,399 | A | 5/1992 | Kovalcheck |
| 5,217,474 | A | 6/1993 | Zacca et al. |
| 5,273,526 | A * | 12/1993 | Dance .......... A61B 17/22 604/35 |
| 5,287,858 | A | 2/1994 | Hammerslag |
| 5,306,244 | A | 4/1994 | Shiber |
| 5,308,354 | A | 5/1994 | Zacca et al. |
| 5,312,427 | A | 5/1994 | Shturman |
| 5,314,438 | A | 5/1994 | Shturman |
| 5,356,418 | A | 10/1994 | Shturman |
| 5,490,859 | A | 2/1996 | Mische |
| 5,584,843 | A | 12/1996 | Wulfman |
| 5,632,755 | A | 5/1997 | Nordgren et al. |
| 5,653,696 | A | 8/1997 | Shiber |
| 5,681,336 | A | 10/1997 | Clement et al. |
| 5,728,129 | A | 3/1998 | Summers |
| 5,779,721 | A | 7/1998 | Nash |
| 5,794,626 | A | 8/1998 | Kieturakis |
| 5,873,882 | A | 2/1999 | Straub et al. |
| 5,876,414 | A | 3/1999 | Straub |
| 5,879,361 | A | 3/1999 | Nash |
| 5,938,670 | A | 8/1999 | Keith et al. |
| 5,938,672 | A | 8/1999 | Nash |
| 5,951,581 | A | 9/1999 | Saadat |
| 5,976,165 | A | 11/1999 | Ball et al. |
| 6,001,112 | A | 12/1999 | Taylor |
| 6,015,420 | A | 1/2000 | Wulfman et al. |
| 6,066,152 | A | 5/2000 | Strauss et al. |
| 6,077,282 | A | 6/2000 | Shturman et al. |
| 6,080,170 | A | 6/2000 | Nash et al. |
| 6,090,118 | A | 7/2000 | McGuckin, Jr. |
| 6,113,615 | A | 9/2000 | Wulfman |
| 6,132,444 | A | 10/2000 | Shturman |
| 6,146,395 | A | 11/2000 | Kanz et al. |
| 6,156,046 | A | 12/2000 | Passafaro et al. |
| 6,156,048 | A | 12/2000 | Wulfman et al. |
| 6,183,487 | B1 | 2/2001 | Barry et al. |
| 6,206,898 | B1 | 3/2001 | Honeycutt et al. |
| 6,270,509 | B1 | 8/2001 | Barry et al. |
| 6,299,623 | B1 | 10/2001 | Wulfman |
| 6,443,967 | B1 | 9/2002 | Kadavy et al. |
| 6,454,779 | B1 | 9/2002 | Taylor |
| 6,482,216 | B1 | 11/2002 | Hiblar et al. |
| 6,491,660 | B2 | 12/2002 | Guo et al. |
| 6,494,890 | B1 | 12/2002 | Shturman et al. |
| 6,497,711 | B1 | 12/2002 | Plaia et al. |
| 6,569,147 | B1 | 5/2003 | Evans et al. |
| 6,569,177 | B1 | 5/2003 | Dillard et al. |
| 6,572,630 | B1 * | 6/2003 | McGuckin, Jr. .......... A61B 17/32075 606/159 |
| 6,579,298 | B1 | 6/2003 | Bruneau et al. |
| 6,579,299 | B2 | 6/2003 | McGuckin, Jr. et al. |
| 6,596,005 | B1 | 7/2003 | Kanz et al. |
| 6,602,264 | B1 | 8/2003 | McGuckin, Jr. |
| 6,626,890 | B2 | 9/2003 | Nguyen et al. |
| 6,632,230 | B2 | 10/2003 | Barry |
| 6,652,546 | B1 | 11/2003 | Nash et al. |
| 6,702,830 | B1 | 3/2004 | Demarais et al. |
| 6,752,630 | B2 | 6/2004 | Roetzer |
| 6,808,531 | B2 | 10/2004 | Lafontaine et al. |
| 6,824,550 | B1 | 11/2004 | Noriega et al. |
| 6,830,577 | B2 | 12/2004 | Nash et al. |
| 6,843,797 | B2 | 1/2005 | Nash et al. |
| 6,905,505 | B2 | 6/2005 | Nash et al. |
| 6,926,725 | B2 | 8/2005 | Cooke et al. |
| 6,936,056 | B2 | 8/2005 | Nash et al. |
| 7,037,316 | B2 | 5/2006 | McGuckin, Jr. et al. |
| 7,172,610 | B2 | 2/2007 | Heitzmann et al. |
| 7,479,147 | B2 | 1/2009 | Honeycutt et al. |
| 7,534,249 | B2 | 5/2009 | Nash et al. |
| 7,645,261 | B2 | 1/2010 | Hinchliffe |
| 7,655,016 | B2 | 2/2010 | Demarais |
| 7,666,161 | B2 | 2/2010 | Nash et al. |
| 7,713,231 | B2 | 5/2010 | Wulfman et al. |
| 7,771,445 | B2 | 8/2010 | Heitzmann et al. |
| 7,833,239 | B2 | 11/2010 | Nash |
| 7,905,896 | B2 | 3/2011 | Straub |
| 7,959,608 | B2 | 6/2011 | Nash et al. |
| 7,976,528 | B2 | 7/2011 | Nash et al. |
| 7,981,128 | B2 | 7/2011 | To et al. |
| 7,981,129 | B2 | 7/2011 | Nash et al. |
| 8,007,506 | B2 | 8/2011 | To et al. |
| 8,062,317 | B2 | 11/2011 | McGuckin, Jr. et al. |
| 8,109,954 | B2 | 2/2012 | Shturman |
| 8,142,458 | B2 | 3/2012 | Shturman |
| 8,226,673 | B2 | 7/2012 | Nash et al. |
| 8,236,016 | B2 | 8/2012 | To et al. |
| 8,323,240 | B2 | 12/2012 | Wulfman et al. |
| 8,348,965 | B2 | 1/2013 | Prudnikov et al. |
| 8,353,922 | B2 | 1/2013 | Noriega |
| 8,353,923 | B2 | 1/2013 | Shturman |
| 8,361,094 | B2 | 1/2013 | To et al. |
| 8,361,097 | B2 | 1/2013 | Patel et al. |
| 8,388,582 | B2 | 3/2013 | Eubanks et al. |
| 8,414,543 | B2 | 4/2013 | McGuckin, Jr. et al. |
| 8,439,937 | B2 | 5/2013 | Montague et al. |
| 8,465,511 | B2 | 6/2013 | McGuckin, Jr. et al. |
| 8,475,484 | B2 | 7/2013 | Wulfman et al. |
| 8,551,128 | B2 | 10/2013 | Hanson et al. |
| 8,568,432 | B2 | 10/2013 | Straub |
| 8,574,249 | B2 | 11/2013 | Moberg |
| 8,579,851 | B2 | 11/2013 | Cull |
| 8,597,313 | B2 | 12/2013 | Thatcher et al. |
| 8,628,549 | B2 | 1/2014 | To et al. |
| 8,628,550 | B2 | 1/2014 | Narveson et al. |
| 8,628,551 | B2 | 1/2014 | Hanson et al. |
| 8,632,557 | B2 | 1/2014 | Thatcher et al. |
| 8,663,259 | B2 | 3/2014 | Levine et al. |
| 8,663,261 | B2 | 3/2014 | Shturman |
| 8,702,735 | B2 | 4/2014 | Rivers |
| 8,758,377 | B2 | 6/2014 | Rivers et al. |
| 8,764,779 | B2 | 7/2014 | Levine et al. |
| 8,795,303 | B2 | 8/2014 | McBroom et al. |
| 8,795,304 | B2 | 8/2014 | Svendsen et al. |
| 8,795,306 | B2 | 8/2014 | Smith et al. |
| 8,882,680 | B2 | 11/2014 | Furlong et al. |
| 8,888,801 | B2 | 11/2014 | To et al. |
| 8,920,402 | B2 | 12/2014 | Nash et al. |
| 9,023,070 | B2 | 5/2015 | Levine et al. |
| 9,028,424 | B2 | 5/2015 | Furlong et al. |
| 9,033,864 | B2 | 5/2015 | Furlong et al. |
| 9,033,895 | B2 | 5/2015 | Furlong et al. |
| 9,050,126 | B2 | 6/2015 | Rivers et al. |
| 9,055,966 | B2 | 6/2015 | Cambronne et al. |
| 9,072,505 | B2 | 7/2015 | Furlong et al. |
| 9,113,945 | B2 | 8/2015 | Malla et al. |
| 9,119,660 | B2 | 9/2015 | Rivers et al. |
| 9,119,661 | B2 | 9/2015 | Rivers et al. |
| 9,211,138 | B2 | 12/2015 | Shturman |
| 9,675,376 | B2 | 6/2017 | To |
| 2002/0007190 | A1 | 1/2002 | Wulfman et al. |

(56) References Cited

U.S. PATENT DOCUMENTS

| | | |
|---|---|---|
| 2002/0099367 A1 | 7/2002 | Guo et al. |
| 2002/0138088 A1 | 9/2002 | Nash |
| 2003/0125757 A1 | 7/2003 | Patel |
| 2003/0199889 A1 | 10/2003 | Kanz et al. |
| 2004/0219028 A1 | 11/2004 | Demarais et al. |
| 2004/0243162 A1 | 12/2004 | Wulfman et al. |
| 2005/0080478 A1 | 4/2005 | Barongan |
| 2005/0119678 A1 | 6/2005 | O'Brien |
| 2005/0149084 A1 | 7/2005 | Kanz et al. |
| 2008/0004643 A1* | 1/2008 | To .................. A61B 17/320758 606/159 |
| 2009/0018565 A1 | 1/2009 | To |
| 2011/0040315 A1 | 2/2011 | To et al. |
| 2011/0106051 A1 | 5/2011 | Saab |
| 2011/0270289 A1 | 11/2011 | To et al. |
| 2012/0071907 A1 | 3/2012 | Pintor et al. |
| 2012/0130410 A1 | 5/2012 | Tal et al. |
| 2012/0211542 A1 | 8/2012 | Racenet |
| 2013/0018398 A1 | 1/2013 | Rivers et al. |
| 2013/0018399 A1 | 1/2013 | Rivers et al. |
| 2013/0023913 A1 | 1/2013 | Rivers et al. |
| 2013/0103046 A1 | 4/2013 | Shiber |
| 2013/0178868 A1 | 7/2013 | Roh |
| 2013/0245704 A1 | 9/2013 | Koltz et al. |
| 2013/0253552 A1 | 9/2013 | Schoenle et al. |
| 2014/0148830 A1 | 5/2014 | Bowman |
| 2014/0200599 A1 | 7/2014 | Shiber |
| 2014/0316451 A1 | 10/2014 | Higgins et al. |
| 2014/0330286 A1 | 11/2014 | Wallace |
| 2015/0051626 A1 | 2/2015 | Rivers et al. |
| 2015/0094748 A1 | 4/2015 | Nash et al. |
| 2015/0164542 A1 | 6/2015 | Wulfman et al. |
| 2015/0245851 A1 | 9/2015 | McGuckin, Jr. |
| 2015/0342682 A1 | 12/2015 | Bowe |

FOREIGN PATENT DOCUMENTS

| | | |
|---|---|---|
| WO | WO 1994/10919 | 5/1994 |
| WO | WO 1998/004199 | 2/1998 |
| WO | WO 2001/19444 | 3/2001 |
| WO | WO 2002/26289 | 4/2002 |
| WO | WO 2008/155759 | 12/2008 |
| WO | WO 2014/91881 | 6/2014 |
| WO | WO 2014/163942 | 10/2014 |

OTHER PUBLICATIONS

The Extended European Search Report Application No. 15200337.2 dated Apr. 28, 2016.

European Search Report for application 17161776.4-1659 dated Jul. 2017.

The Extended European Search Report Application No. 16187574.5 dated Jan. 30, 2017.

* cited by examiner

ATHERECTOMY DEVICE

This application claims is a divisional of application Ser. No. 14/616,670, filed on Feb. 7, 2015, which claims priority from provisional application Ser. No. 61/946,733, filed Mar. 1, 2014. The entire contents of each of these applications are incorporated herein by reference.

BACKGROUND

Technical Field

This application relates to a vascular surgical apparatus, and more particularly to a minimally invasive device for removing plaque or other deposits from the interior of a vessel.

Background of Related Art

The vascular disease of atherosclerosis is the buildup of plaque or substances inside the vessel wall which reduces the size of the passageway through the vessel, thereby restricting blood flow. Such constriction or narrowing of the passage in the vessel is referred to as stenosis. In the case of peripheral vascular disease, which is atherosclerosis of the vascular extremities, if the vessel constriction is left untreated, the resulting insufficient blood flow can cause claudication and possible require amputation of the patient's limb. In the case of coronary artery disease, if left untreated, the blood flow through the coronary artery to the myocardium will become inadequate causing myocardial infarction and possibly leading to stroke and even death.

There are currently several different treatments for treating arterial disease. The most invasive treatment is major surgery. With peripheral vascular diseases, such as occlusion of the tibial artery, the major surgery involves implantation and attachment of a bypass graft to the artery so the blood flow will bypass the occlusion. The surgery involves a large incision, e.g. a 10 inch incision in the leg, is expensive and time consuming for the surgeon, increases patient pain and discomfort, results in a long patient recovery time, and has the increased risk of infection with the synthetic graft.

Major surgery for treating coronary artery disease is even more complex. In this surgery, commonly referred to as open heart surgery, a bypass graft connects the heart to the vessel downstream of the occlusion, thereby bypassing the blockage. Bypass surgery requires opening the patient's chest, is complex, has inherent risks to the patient, is expensive and requires lengthy patient recovery time. Bypass surgery also requires use of a heart lung machine to pump the blood as the heart is stopped, which has its own risks and disadvantages. Oftentimes, the saphenous vein in the patient's leg must be utilized as a bypass graft, requiring the additional invasive leg incision which further complicates the procedure, increases surgery time, lengthens the patient's recovery time, can be painful to the patient, and increases the risk of infection.

Attempts to minimize the invasiveness of coronary bypass surgery are currently being developed and utilized in certain instances. These typically include cracking a few ribs and creating a "window approach" to the heart. Although the window approach may reduce patient trauma and recovery time relative to open heart surgery, it still requires major surgery, and is a complicated and difficult surgery to perform due to limited access and limited instrumentation for successfully performing the operation. Attempts to avoid the use of a heart lung machine by using heart stabilization methods is becoming more accepted, but again, this does not avoid major surgery.

Due to these problems with major peripheral or coronary vascular surgery, minimally invasive procedures have been developed. Balloon angioplasty is one of the minimally invasive methods for treating vessel occlusion/obstructions. Basically, a catheter having a balloon is inserted through the access artery, e.g., the femoral artery in the patient's leg or the radial artery in the arm, and advanced through the vascular system to the occluded site over a wire. The deflated balloon is placed at the occlusion and the balloon is inflated to crack and stretch the plaque and other deposits to expand the opening in the vessel. Balloon angioplasty, especially in coronary surgery, is frequently immediately followed by insertion of a stent, a small metallic expandable device which is placed inside the vessel wall to retain the opening which was created by the balloon. Balloon angioplasty has several drawbacks including difficulty in forcing the balloon through the partially occluded passageway if there is hard occlusion, the risk involved in cutting off blood flow when the balloon is fully inflated, and the frequency of restenosis after a short period of time since the plaque is essentially stretched or cracked and not removed from the vessel wall or because of the development of intimal hyperplasia.

Another minimally invasive technique used to treat arteriosclerosis is referred to as atherectomy and involves removal of the plaque by a cutting or abrading instrument. This technique provides a minimally invasive alternative to bypass surgery techniques described above as well as can provide an advantage over balloon angioplasty methods in certain instances. Atherectomy procedures typically involve inserting a cutting or ablating device through the access artery, e.g., the femoral artery or the radial artery, advancing it through the vascular system to the occluded region, and rotating the device at high speed to cut through or ablate the plaque over the wire. The removed plaque or material can then be suctioned out of the vessel or be of such fine diameter that it is cleared by the reticuloendothelial system. Removal of the plaque in an atherectomy procedure has an advantage over balloon angioplasty plaque displacement since it debulks the material.

Examples of atherectomy devices in the prior art include U.S. Pat. Nos. 4,990,134, 5,681,336, 5,938,670, and 6,015,420. These devices have elliptical shaped tips which are rotated at high speeds to cut away the plaque and other deposits on the interior vessel wall. A well-known device is marketed by Boston Scientific Corp. and referred to as the Rotablator. As can be appreciated, in these devices, the region of plaque removal is dictated by the outer diameter of the cutting tip (burr) since only portions of the plaque contacted by the rotating tip are removed. Obviously, the greater the area of plaque removed, the larger the passageway created through the vessel and the better the resulting blood flow.

Since these atherectomy tips need to be inserted through an introducer sheath or catheter to the target site, the larger the tip, the larger the diameter of the introducer sheath required. However, larger introducer sheaths increase the risk of trauma to the patient, are harder to navigate through the vessels, and create larger incisions (require larger puncture sites) into the access artery which cause additional bleeding and complicate closure of the incision at the end of the procedure. On the other hand, if smaller introducer sheaths are utilized, then the rotating atherectomy tip also has to be of a smaller dimension to fit within the sheath, but such smaller tip might not be able to remove a sufficient area of obstructive deposits and the vessel could remain partially occluded. Thus, a tradeoff must be made between these two opposing goals: larger cutting tip and smaller introducer sheath.

This problem was recognized for example in U.S. Pat. Nos. 5,217,474 and 6,096,054 which attempted solutions involved expandable cutting tips. These tips however are quite complex and require additional expansion and contraction steps by the surgeon.

U.S. Pat. No. 6,676,698 discloses an atherectomy device designed to solve the foregoing problems of the prior art. The device attempted to provide an improved atherectomy cutting tip to obtain an optimal balance between the competing objectives of the smallest introducer sheath size to facilitate insertion and reduce trauma to the vessel and the largest atherectomy tip size to remove a larger region of plaque or other deposits from the vessel wall.

However it would be advantageous to enhance removal of the small particles once broken off by the atherectomy tip of the '698 patent.

SUMMARY

The present invention provides in one aspect a surgical system for removing deposits such as plaque from an interior of a vessel comprising:
 an atherectomy device having
 an outer member;
 a rotatable tip extending distally from the outer member and having an internal distal surface and a plurality of openings; and
 a rotatable shaft positioned within the outer member and having a longitudinal axis and a distal opening, the tip mounted to a distal portion of the rotatable shaft, the tip being rotatable about its longitudinal axis upon rotation of the shaft about its longitudinal axis to remove deposits from the interior of the vessel, the rotatable shaft including a series of outer threads dimensioned to direct deposits (particles) proximally;
 an introducer, the atherectomy device insertable through the introducer to access a target vessel containing the deposits;
 a motor for rotating the rotatable shaft and the tip;
 a suction device for aspirating deposits through the plurality of openings in the rotatable tip and through a gap between the rotatable shaft and the outer member to direct proximally deposits dislodged by the rotating tip; and
 a fluid injection device for injecting high pressure fluid through the rotatable shaft, the fluid exiting the distal opening in the rotatable shaft and contacting the internal distal surface of the rotatable tip where it is directed rearwardly to direct proximally deposits dislodged by the rotatable tip.

In some embodiments, a distal portion of the rotatable tip has a bullet shaped nose. In some embodiments, a plurality of longitudinally extending grooves are formed in an outer surface of the rotatable tip to form an ablation surface. In some embodiments, the rotatable tip has a scalloped region at the intermediate portion.

In some embodiments, the introducer has a side arm connectable to a source of suction so that deposits can be aspirated in the gap between the outer member and introducer sheath.

In accordance with another aspect, the present invention provides an atherectomy apparatus for removing deposits such as plaque from an interior of a vessel, comprising:
 an outer member;
 a rotatable shaft positioned for rotational movement within the outer member, the shaft having a lumen extending therethrough dimensioned to receive a guidewire and a distal opening communicating with the lumen, the lumen having a cross-sectional dimension to enable fluid injection between an inner diameter of the shaft and an outer diameter of the guidewire; and
 a tip having a longitudinal axis and mounted to the rotatable shaft for rotation about its longitudinal axis upon rotation of the rotatable shaft, the tip mounted to a distal portion of the rotatable shaft such that the distal opening of the rotatable shaft is axially spaced from a distal internal surface of the tip such that fluid injected through the lumen of the rotatable shaft contacts the distal internal surface of the tip and is redirected proximally to direct in a proximal direction deposits (particles) removed by the rotational movement of the tip, the tip including a guidewire lumen for receiving the guidewire to enable over the wire insertion of the apparatus.

In some embodiments, the tip has an intermediate portion between distal and proximal portions, and a scalloped portion at the intermediate portion. In some embodiments, the rotatable shaft has a threaded region to direct deposits proximally as the shaft is rotated.

In accordance with another aspect, the present invention provides a method for removing deposits such as plaque from an interior of a vessel comprising the steps of:
 providing an introducer sheath having an internal diameter;
 providing a deposit removal device including a rotating shaft and a rotating tip at a distal portion of the rotating shaft, the rotating tip having an outer diameter greater than the internal diameter of the introducer sheath and further having first and second opposing narrowed regions, the rotating shaft having an external screw thread;
 inserting the introducer sheath through a skin incision and into a vessel, the introducer sheath forming an incision opening at least equal to an external diameter of the introducer sheath;
 advancing the rotating tip adjacent the deposits to be removed;
 actuating a motor to rotate the rotating tip at high speed to contact and remove the deposits from the vessel and to rotate the rotating shaft such that the external screw thread of the rotating shaft directs deposits proximally;
 injecting fluid through the rotating shaft to contact an inner surface of the rotating tip wherein the fluid is redirected proximally to direct proximally the deposits removed by the rotational movement of the rotating tip; and applying a vacuum to aspirate proximally deposits removed by rotational movement of the rotating tip.

In some embodiments, the method further comprises the steps of inserting the rotating tip into the introducer sheath to deform the introducer sheath to accommodate a larger outer diameter of the rotating tip, and advancing the rotating tip out through a distal opening in the introducer sheath, thereby allowing the introducer sheath to return to its undeformed configuration.

In some embodiments, the device includes an outer member and the rotating shaft is rotatably positioned within the outer member and particles are aspirated proximally in a gap between an outer diameter of the rotating shaft and an inner diameter of the outer member. In some embodiments, in addition or as an alternative to aspiration in the gap between the shaft and the outer member, the deposits are aspirated proximally in a gap between an outer diameter of the outer member and an inner diameter of the introducer sheath.

The method can further include the step of inserting the rotating tip over a guidewire. In some embodiments, step of injecting fluid injects high pressure fluid in a gap between an inner diameter of the rotating shaft and an outer diameter of the guidewire inserted through the inner shaft.

In some embodiments, the method includes the step of removing the deposits through side openings in the rotating tip.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1:
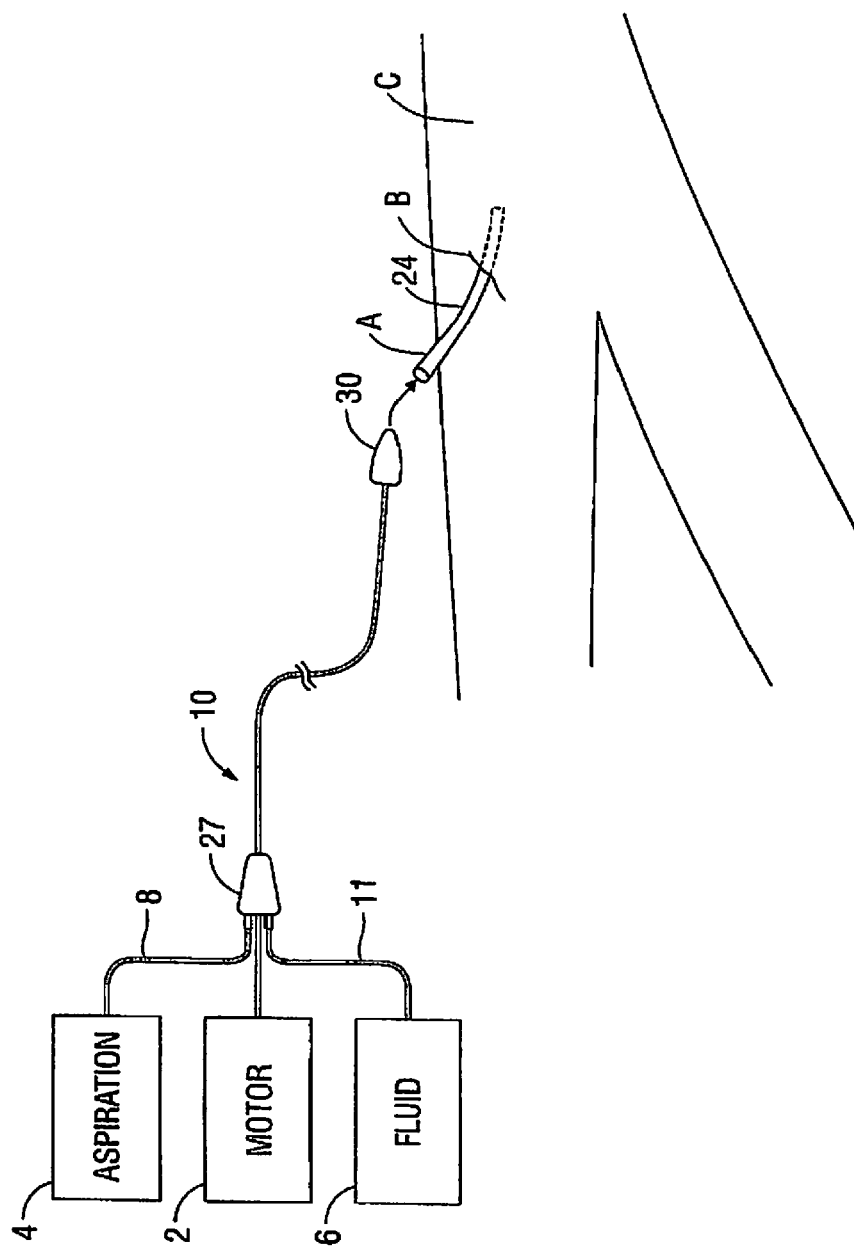
FIG. 1 is a schematic view of one embodiment of the atherectomy system of the present invention.
Figure 2:
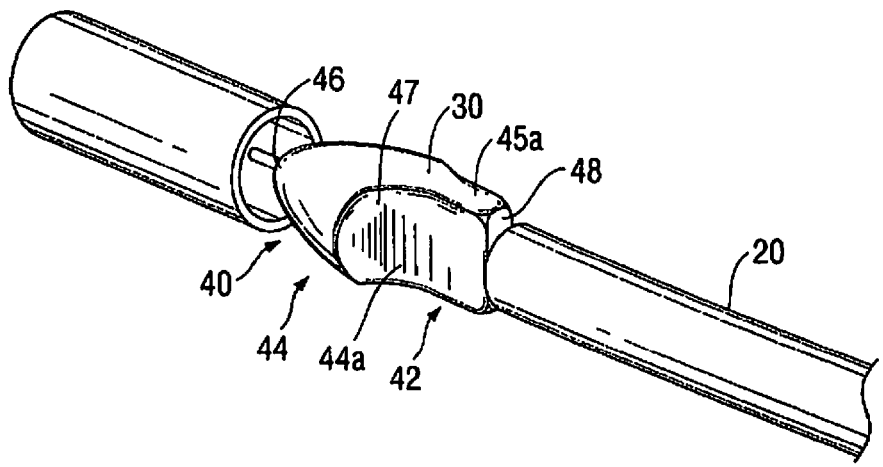
FIG. 2 is a perspective view of the distal end of the atherectomy device of the present invention prior to introduction into an introducer sheath.

The present invention is directed to an atherectomy tip designed for high speed rotation to remove plaque or other deposits on the inside wall of the vessel to widen the blood passageway therethrough. To achieve such rotation, the rotatable atherectomy tip is positioned at a distal end of a flexible rotating shaft that can be gas or electrically powered. The shaft rotates at high speed, typically between 100,000 and 200,000 rpm, causing the cutting or ablation surface of the tip to remove the plaque and deposits to which it comes into contact. The atherectomy tip of the present invention has application in a variety of vessels such as the coronary arteries, peripheral vessels such as the tibial artery, femoral, and popliteal, and saphenous vein bypass grafts.

In order for the atherectomy tip to reach the vessel stenosis (obstruction) it is inserted along with the flexible shaft through an introducer sheath and over a guidewire. More specifically, the introducer sheath is placed through a skin incision and into a vessel, e.g., the femoral artery in the patient's leg, to provide access to the target site. A guidewire is then inserted through the introducer sheath and advanced through the appropriate vessels to the target obstructed site, typically the coronary artery. The flexible shaft and attached atherectomy tip are then inserted through the introducer sheath and threaded over the length of the guidewire to the target obstructed site. Actuation of the motor spins the shaft and tip so the cutting surface repeatedly comes into contact with the obstruction, e.g., plaque, to remove it from the vessel wall. In the alternate embodiment described below, a sheath can be advanced intravascularly to the target site, with the atherectomy device inserted through the sheath emerging at the target site.

The atherectomy device of the present invention provides several features to remove the particles (deposits) dislodged by the high speed rotational movement of the rotatable atherectomy tip. The features include one or more of the following: 1) holes in the atherectomy tip to receive the dislodged particles and a vacuum to aspirate the particles through the holes in the atherectomy tip; 2) a vacuum to aspirate particles through a gap between the rotating shaft and the outer tube (member) of the device; 3) a vacuum to aspirate particles through a gap between the outer tube of the device and the introducer sheath; 4) a screw thread on the rotating shaft to direct particles rearwardly as the shaft is rotated; and/or 5) fluid injection in the gap between the atherectomy shaft and guidewire which contacts an internal end wall of the atherectomy tip and is directed rearwardly. Each of these features will be described in more detail below.

The atherectomy tip of the present invention is configured for placement through a smaller sized introducer sheath without sacrificing the region of plaque it is capable of removing. This is achieved through the circumferential and diametrical relationship of the tip at various sections along its length. The advantages of utilizing a smaller sized sheath, as enumerated above in the Background Section of this application, are it is less traumatic to the vessel, reduces the amount of bleeding, reduces the risk of infection and eases closure of the vessel at the end of the procedure.

As can be appreciated, the atherectomy tips of the prior art require a sheath size which is greater in diameter than the tip diameter. The largest diameter of the tip also dictates the region of plaque which can be removed, since as the tip rotates at high speeds, it only cuts the plaque which comes into contact with the outermost surface.

The present invention will now be described with detailed reference to the drawings wherein like reference numerals identify similar or like components throughout the several views.

Figure 3:
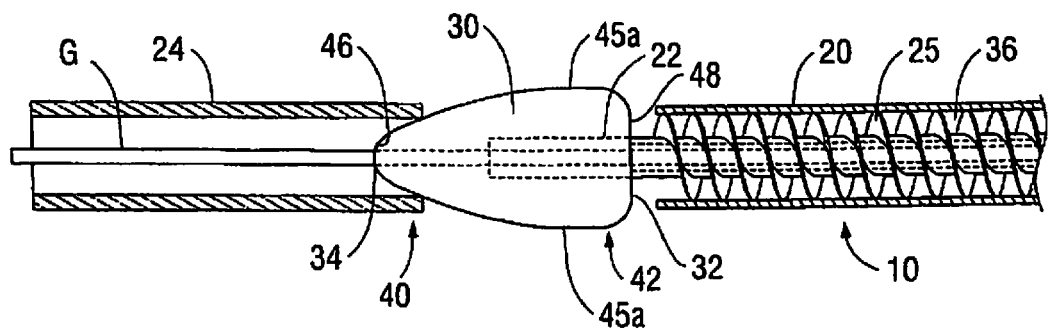
FIG. 3 is a side view in partial cross-section of the atherectomy device of FIG. 2 being inserted into an introducer sheath.
Figure 4:
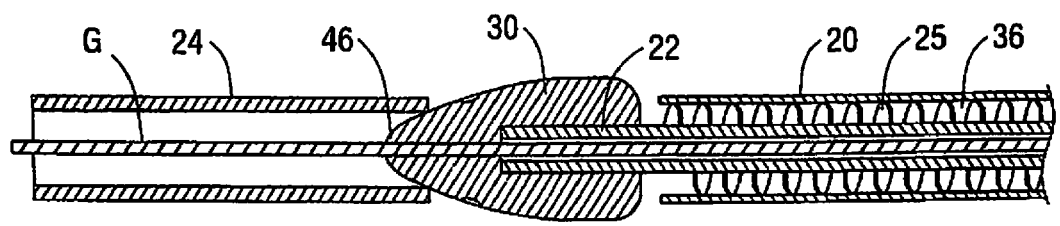
FIG. 4 is a cross-sectional view of the atherectomy device being inserted into the introducer sheath.
Figure 5:
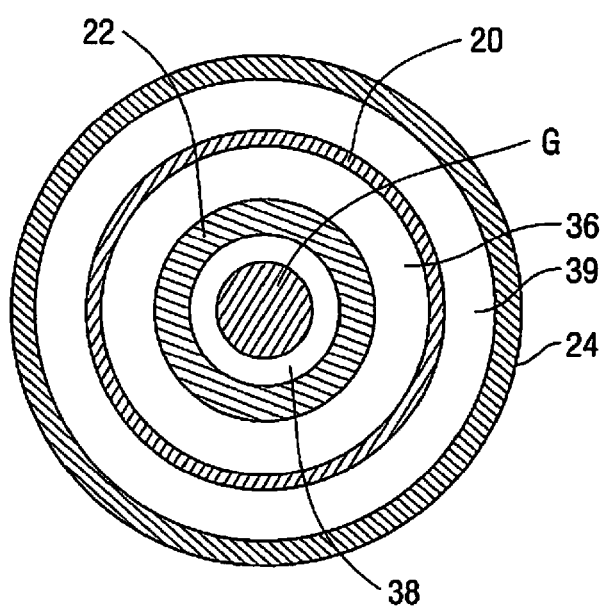
FIG. 5 is transverse cross-sectional view of the atherectomy device within the introducer sheath.
Figure 6:
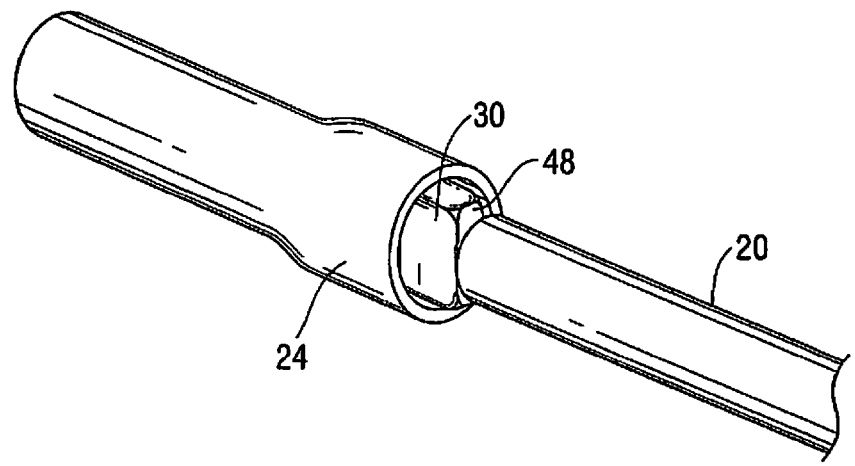
FIG. 6 is a perspective view of the distal end of the atherectomy device inserted into the introducer sheath.
Figure 7:
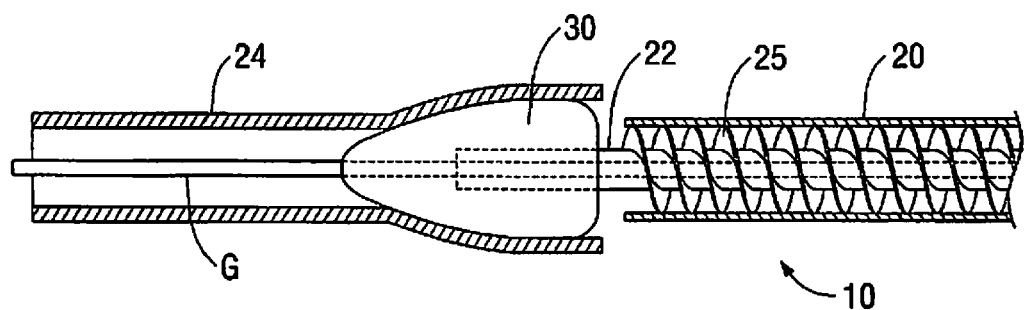
FIG. 7 is a side view in partial cross-section of the atherectomy device inserted into the introducer sheath.
Figure 8:
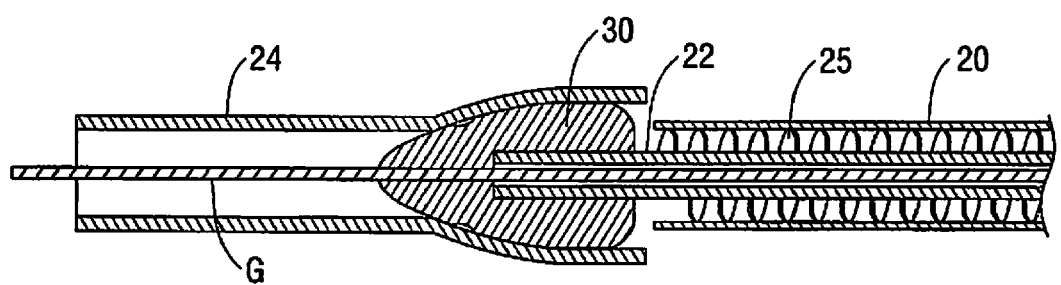
FIG. 8 is a cross-sectional view of the atherectomy device inserted into the introducer sheath.

FIG. 1 illustrates one embodiment of a system for causing rotation of the tip 30, the system shown schematically. The atherectomy tip 30 of the device 10 is connected to the distal end of the flexible inner shaft 22 (see FIG. 3) such that rotation of the inner shaft 22 rotates the rotatable tip 30. The rotatable shaft 22, with burr or tip 30 at its distalmost end, is electrically powered for high speed rotation to rotate the shaft 22 and tip 30. High speed rotation of the shaft 22 likewise rotates tip 30, enabling the tip 30 to break up plaque to treat stenosis of a vessel. A motor housing 2, shown schematically, contains a motor mounted therein and a motor shaft (not shown). The atherectomy device or catheter 10 is operatively connected to the motor housing 2 such that activation of the motor rotates the inner shaft 22 of the catheter. A control knob can be provided to adjust the rotational speed of the shaft 22 and tip 30, and a window can be provided to visually display the speed. An advancing mechanism (not shown) can be provided for sliding the shaft 22 and tip 30 a desired distance within the vessel (e.g., about 3-10 cm). Shaft 22 and tip 30 can be disposable. As shown for illustrative purposes, introducer sheath or catheter 24 is inserted through an incision "A" in the patient's leg, and through an incision "B" in the femoral artery "C". The shaft 22 and tip 30 are then introduced through the introducer sheath 24 into the femoral artery "C", and advanced to the target artery, e.g., the coronary artery to the treatment obstruction site. Note that a guidewire (not shown) extends through the sheath 24 and into the target artery so that the shaft 22 and tip 30 are inserted over the guidewire.

The system further includes an aspiration source and fluid source, shown schematically, and respectively designated by reference numerals 4 and 6. Tubing 8 extends from the aspiration source 4 to the catheter 10, preferably through a side arm of catheter hub 27 for aspiration between an outer wall of the shaft and inner wall of outer tube (member) 20 of catheter 10. Tubing 11 extends from the fluid source 6, preferably through a second side arm of hub 27, to communicate with the inner lumen of the shaft 22, in the space (gap) between the guidewire and inner wall of shaft 22.

Figure 17:
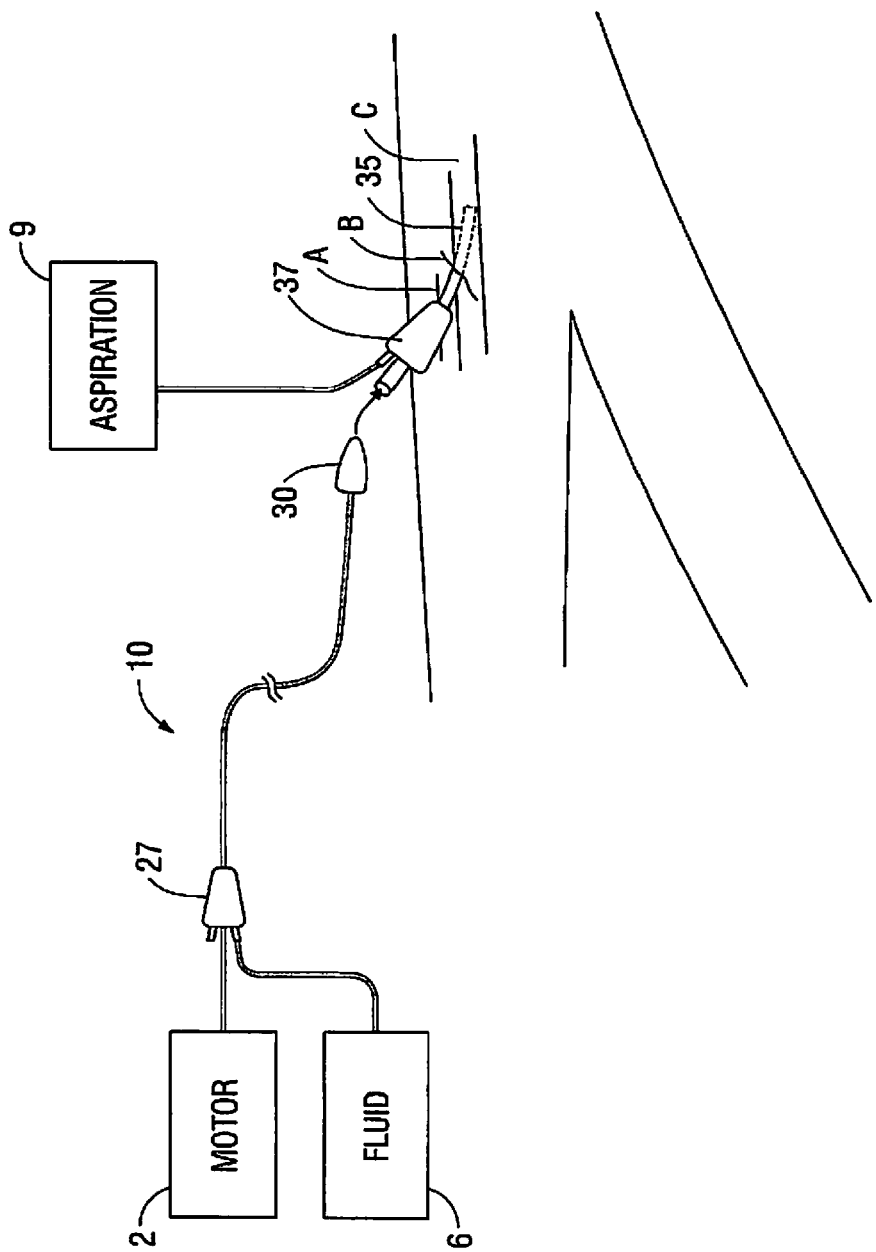
FIG. 17 is a schematic view of an alternative embodiment of the atherectomy system of the present invention.

In an alternate embodiment of FIG. 17, the system, shown schematically, is identical to the system of FIG. 1, except it has an aspiration source 9 communicating with the introducer sheath 35 via a port or side arm in hub 37 to provide aspiration in the space (gap) between the inner wall of the introducer sheath 35 and the outer wall of outer tube 20 of catheter 10. This is explained in more detail below. The introducer sheath 35 can extend to a region adjacent the tip or alternatively a sleeve would be inserted through the introducer sheath 24 and advanced over the guidewire. Note the aspiration through the introducer sheath 35 can be the sole source of aspiration or alternatively used in addition to the aspiration through the catheter as in FIG. 1.

It should be appreciated that the rotatable (rotating) tip 30 is shown inserted through the femoral artery by way of example as other vessels can be utilized for access, such as the radial artery. Also, the tip 30 of the present invention (and other tips described herein) can be used to remove plaque or other obstructions in a variety of vessels such as the coronary artery, the tibial artery, the superficial femoral, popliteal, saphenous vein bypass grafts and instent restenosis.

Turning now to FIGS. 2-13, the first embodiment of the atherectomy tip 30 of the present invention will now be described in more detail. Tip or burr 30 has a front (distal) portion (section) 40, a rear (proximal) portion (section) 42, and an intermediate portion (section) 44. These portions vary in transverse cross-section as can be appreciated by the Figures. Thus, the front portion 40 can be defined for convenience as the area starting at the distalmost end 46, terminating at the scalloped region, and forming a bullet-nose configuration. The cross-section of the front portion 40 in one embodiment is substantially circular in configuration. Note the term "distal" refers to regions father from the user and the term "proximal" refers to regions closer to the user.

Intermediate portion 44 can be considered for convenience as starting at the scalloped portion (proximal of the proximal end of the front portion 40) and terminating at the proximal end of the scalloped region. The cross-section of the intermediate portion 44 progressively changes from substantially circular, to an elongated shape having two substantially flat (substantially linear) opposing sidewalls 44a. As can be appreciated, the elongation progressively increases in a first dimension while progressively narrowing in a second dimension. Thus, the distance between opposing linear walls 44a is less than the distance between opposing arcuate walls 45a, with the distances between linear walls 44a decreasing toward rear section 42.

Rear portion 42 can be considered to begin, for convenience, at the proximal end of the scalloped region of the intermediate portion 44, and terminate at the proximalmost edge 48 of tip 30. The rear portion 42 preferably has the same elongated cross-sectional dimension throughout its length, with substantially linear walls 44a separated by a distance less than the distance between opposing curved walls 45a.

It should also be appreciated that the front, intermediate and rear portions/sections are designated for convenience and are not intended to necessarily denote three separate segments connected together. Rotatable tip 30 is preferably a monolithic piece.

Figure 14:
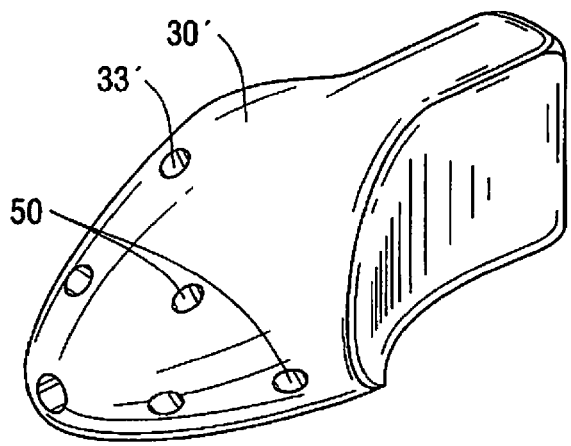
FIG. 14 is a front perspective view of an alternate embodiment of the rotating tip of the present invention having additional openings for particle removal.
Figure 15:
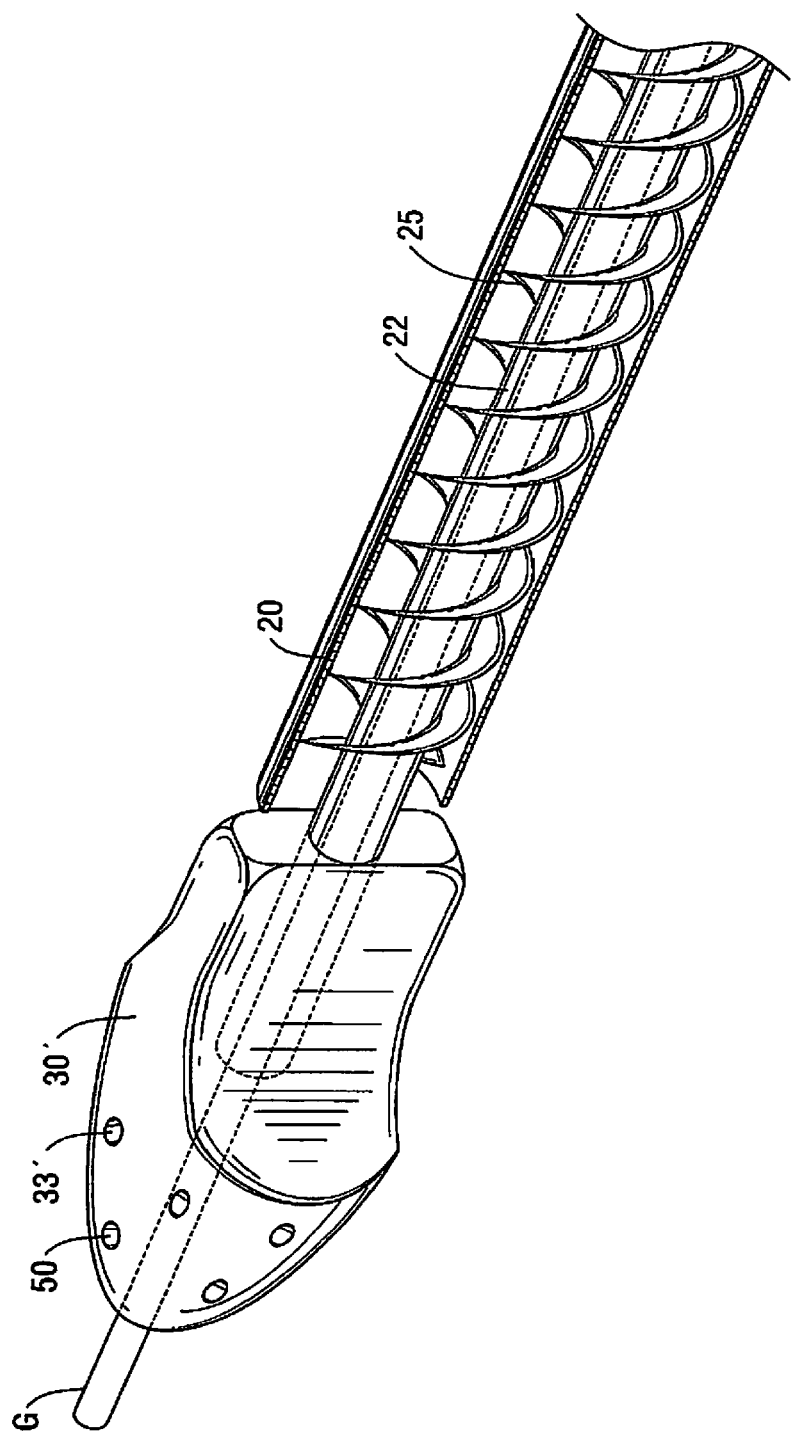
FIG. 15 is a perspective view illustrating the rotating shaft and tip of the atherectomy device of FIG. 14 inserted over a guidewire.

Tip 30 has a proximal or rear (proximal) opening 32 and a front (distal) opening 34 connected by a lumen. The flexible shaft 22 is inserted through rear opening 32 and attached to the tip 30 within lumen 36, however, terminating proximally of the distalmost end 46 of the tip 30 so as to leave a path for high pressure fluid flow. A guidewire G can extend through the hollow flexible shaft 22 and through front opening 34 of tip 30 to enable over the wire insertion of the atherectomy tip 30. One or more openings 33 could be provided in the tip 30 to enable removal of the plaque as the particles (deposits) can be aspirated through the openings 33 by the aspiration source 4. Note FIGS. 14 and 15 illustrate an alternate embodiment of the tip, designated by reference numeral 30', having openings 33' identical to openings 33 of FIG. 12, plus additional openings 50 for aspiration of particles. In all other respects, tip 30' is identical to tip 30. Tip 30' is shown with the shaft 22 and outer member 20 positioned over a guidewire G in FIG. 15 discussed below. Note deposits and particles are used interchangeably herein.

A scalloped or narrowed section 47 is formed in both sides in the intermediate section 44 of the tip 30 to reduce the profile of the tip 30. These scalloped sections form the aforedescribed opposing substantially linear walls. By reducing the profile, i.e., the diameter and circumference, the atherectomy tip of the present invention could be inserted through smaller introducer sheaths than would otherwise be the case if the circumference increased with increasing diameter.

The region of plaque removal is defined by the largest diameter region of the tip since the tip is rotating at high speeds and the plaque is cut or abraded only where the tip comes into contact with it. However, the sheath size required is determined by the largest circumference region of the tip.

As a result of these scalloped sections, as the diameter of tip 30 increases in one orientation, it decreases in the transverse orientation, enabling the circumference to remain constant. Since the diameter is reduced in one transverse orientation, the tip 30 can be introduced into an introducer sheath have an internal diameter slightly less than the largest diameter of the tip, since the sheath has room to deform because of the reduced regions, i.e., the scalloped sections, of the tip 30. In the prior art elliptical tip, the rounded symmetrical configuration leaves no room for the sheath to deform so the sheath size must exceed the largest diameter region.

As can be appreciated, the tip 30 of the present invention can fit into conventional introducer sheaths having an internal diameter less than the largest outer diameter of the tip 30. This can be achieved by the fact that the tip 30 can deform the internal walls of the introducer sheath 24 as it is inserted, by elongating it in the direction shown in FIGS. 7 and 8. If the scalloped walls were not provided, the sheath could not deform because it would be limited by the width of the tip as described below.

Another way to view the tip 30 is that for a given catheter French size desired to be used by the surgeon, a larger atherectomy tip can be utilized if the atherectomy tip 30 of the present invention is selected instead of the prior art elliptical tip, thereby advantageously increasing the region of plaque removal to create a larger passageway in the vessel.

In alternate embodiments of the tip 30, longitudinal or elongated circular and oval cutting grooves could be provided to provide a roughened surface to cut or ablate the plaque as the tip is rotated. The grooves or indentations can be formed by laser cutting a series of grooves extending longitudinally within the interior of the tip stock. The tip is then ground to remove portions of the outer surface to partially communicate with the grooves, thereby creating indentations forming a roughened surface for contact with the plaque. The resulting formation is a series of elongated cutouts/indentations on the front and intermediate portions and oval shaped cutouts/indentations on the distal and intermediate portions.

Another way contemplated to create the roughened surface is by blasting, e.g., sandblasting or grit blasting, the tip. The tip is held in a fixture and blasted at a certain pressure, thereby removing portions of the outer surface to create a roughened surface. Creation of a roughened surface by chemical etching is also contemplated.

Shaft 22 can include a series of threads 25. These threads function as an Archimedes screw, i.e., a screw pump, to remove the particles/deposits dislodged by the tip 30. That is, as the shaft 22 is rotated, the screw's helical surface scoops the deposits and directs the deposits proximally (rearwardly) along the shaft 22. The aspiration in the space between shaft 22 and outer member 20 pulls dislodged particles proximally. The Figures show the threads almost abutting the outer member 20 but in preferred embodiments the threads would be spaced further inwardly from the outer member to leave space for rotation and aspiration.

Figure 9:
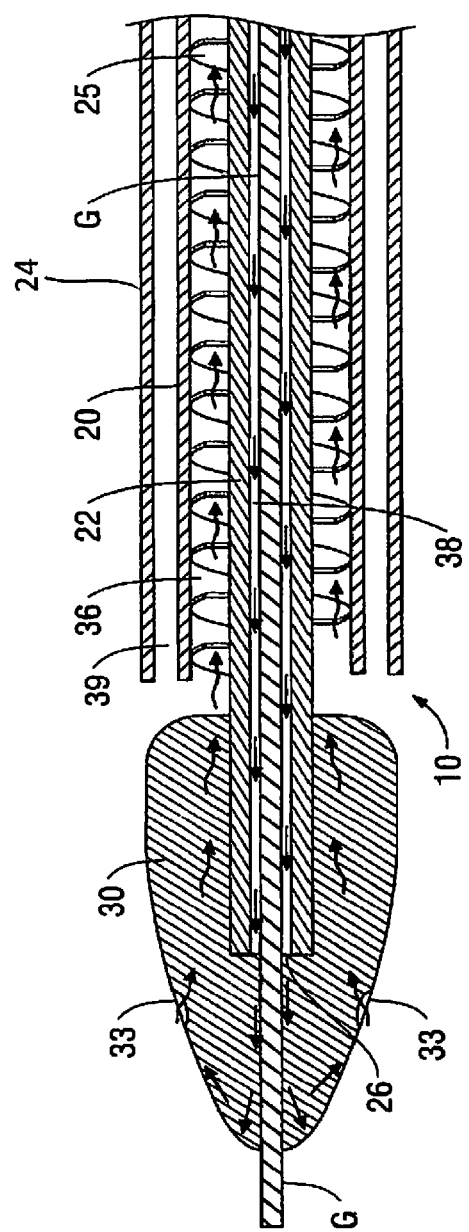
FIG. 9 is a side cross-sectional view of the distal portion of the atherectomy device of FIG. 2 illustrating fluid and particle flow.
Figure 10:
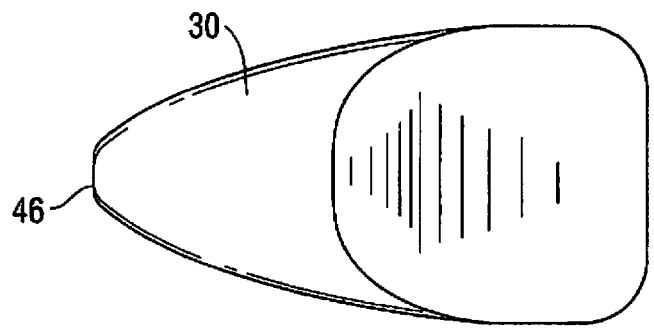
FIG. 10 is a top view of the rotating tip (head) of the atherectomy device.
Figure 11:
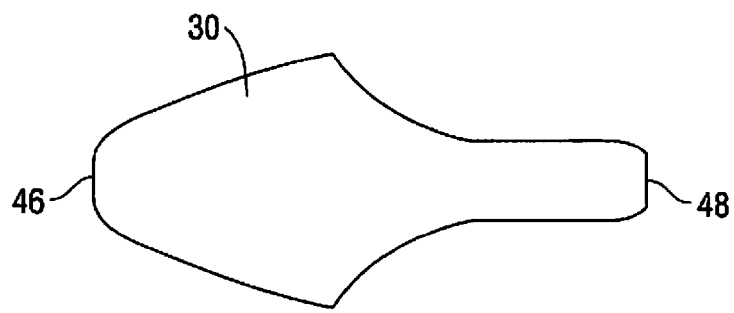
FIG. 11 is a side view of the rotating tip of the atherectomy device.
Figure 12:
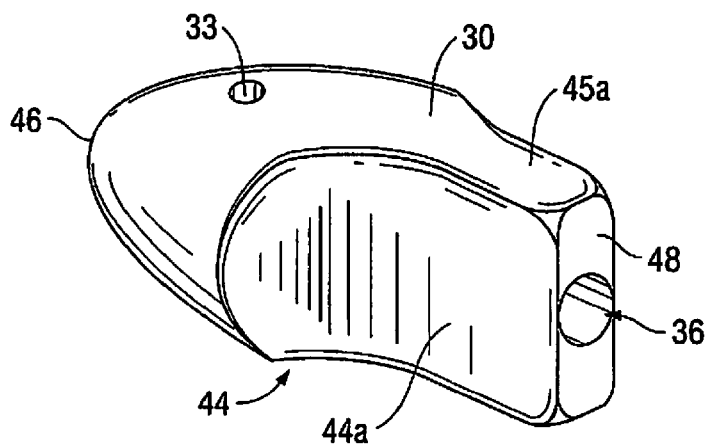
FIG. 12 is a rear perspective view of the rotating tip of the atherectomy device.
Figure 13:
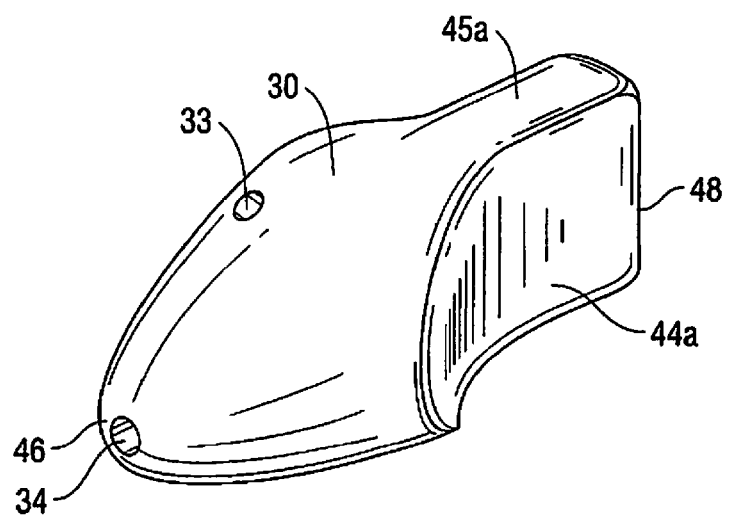
FIG. 13 is a front perspective view of the rotating tip of the atherectomy device.

The system of the present invention, as noted above, includes an aspiration system and a fluid system. The aspiration system 4 provides suction through the shaft 22, in the gap 36 between the outer diameter of the shaft 22 and the inner diameter of the outer member (outer tube) 20 of catheter 10 when the aspiration system 4 is activated. Fluid can be pumped at high pressure into the gap between the outer diameter of the guidewire G and the inner diameter of the shaft 22. In this manner, as shown in FIG. 9, fluid injected from fluid source 6 flows through the gap 38 between the inner wall of the lumen of the shaft 22 and the outer wall of the guidewire G. The fluid exits opening 26 in shaft 22 to flow through an inner lumen of the tip 30 and into contact with the internal end wall of the tip 30, where it is then directed back, as shown by the solid arrows in FIG. 9, thereby providing a proximal force on the particles to force the particles rearwardly (proximally) through the gap 36 between the shaft 22 and outer member 20, with the rotating helical screw further directing the particles (deposits) rearwardly (proximally). Also, particles are aspirated through openings 33 in tip 30, and directed rearwardly in the gap 36 between the shaft 22 and outer tube 20 as indicated by the squiggly arrows of FIG. 9. Note in this embodiment of FIG. 9, which utilizes the system of FIG. 1, aspiration is not provided in the gap 39 between the outer member 20 of catheter 10 and the introducer sheath 24. However, in the embodiment utilizing the system of FIG. 17, aspiration is provided in the gap 39 between the introducer sheath 24 and catheter 10, and this is shown in FIG. 16C described below.

Figure 16A:
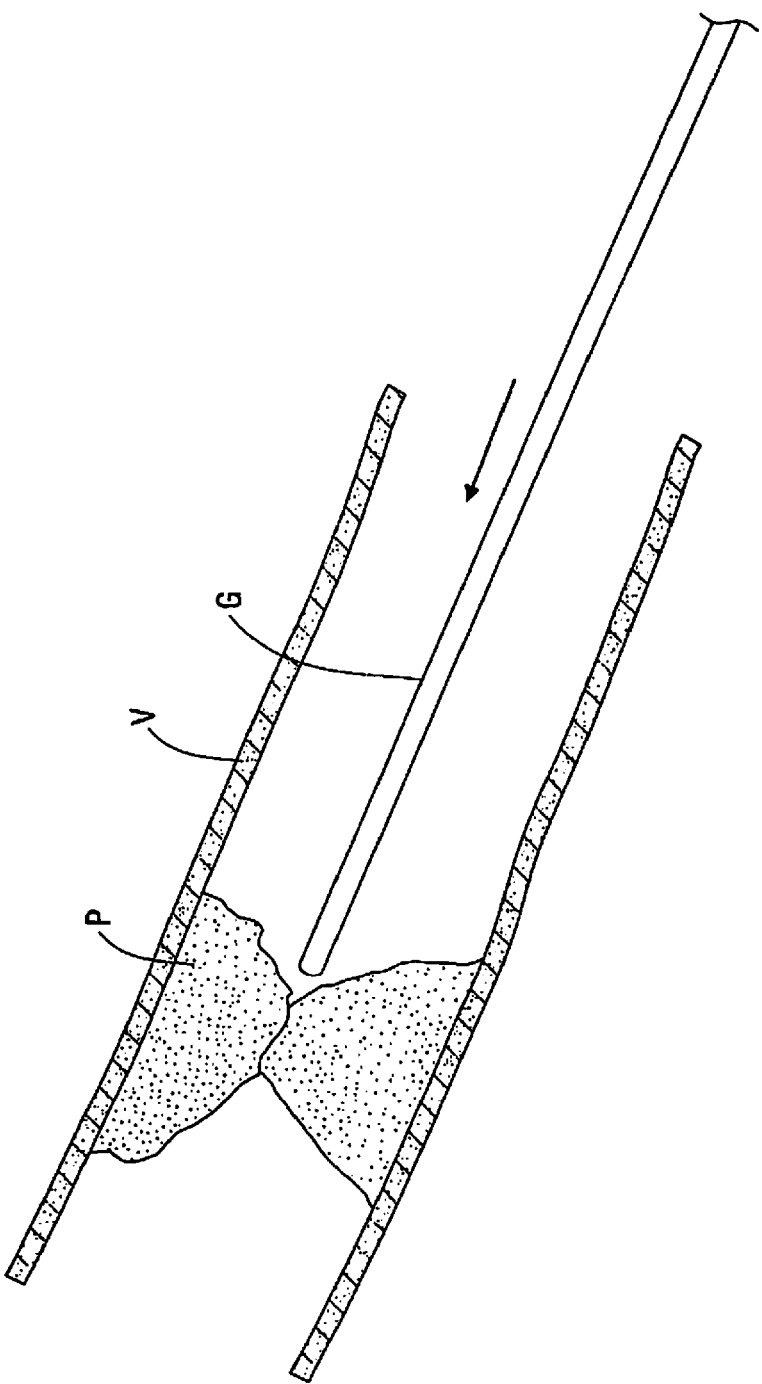
FIG. 16A is a perspective view showing the guidewire advanced into the vessel adjacent the plaque to be removed.
Figure 16B:
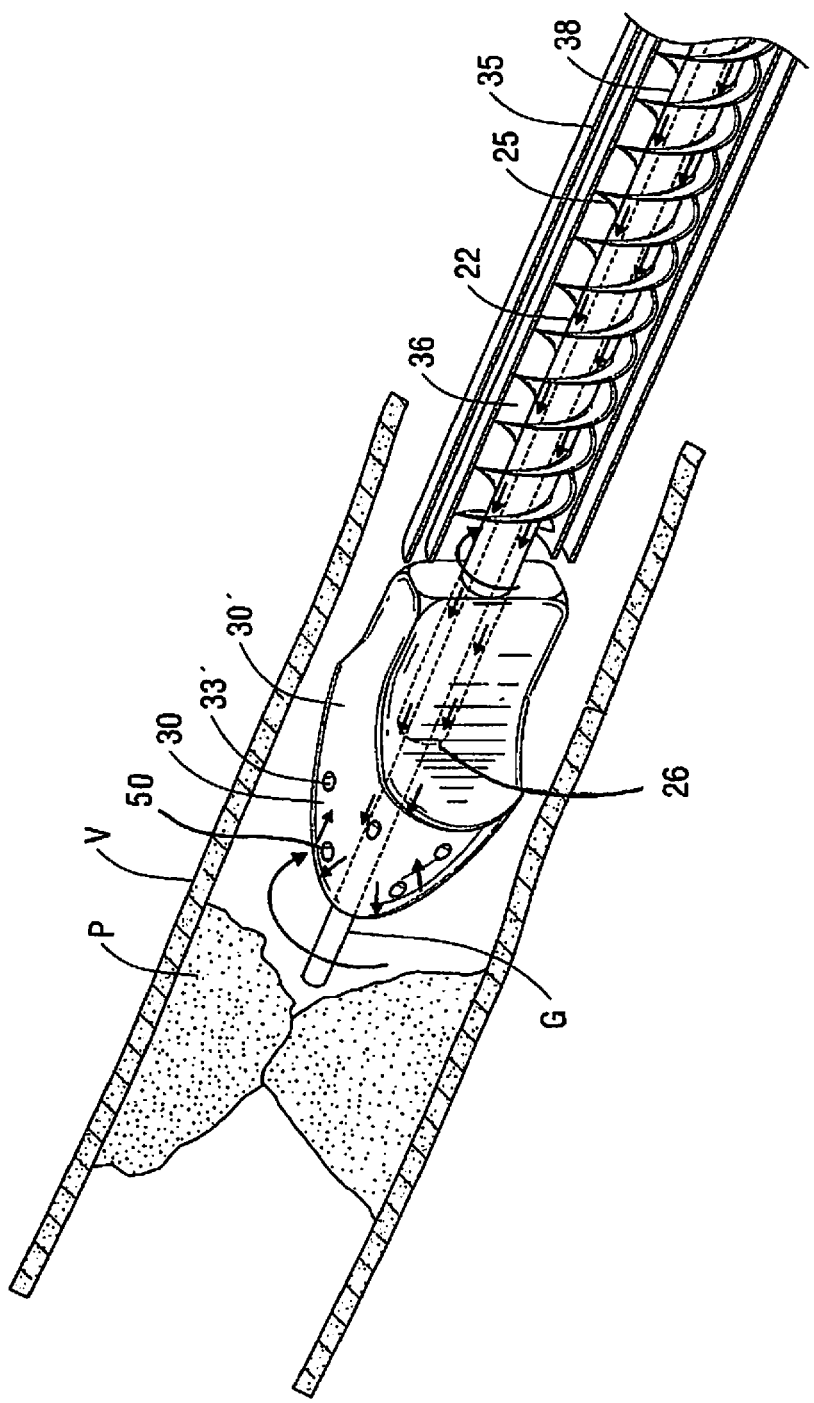
FIG. 16B is a perspective view of the atherectomy device of FIG. 15 inserted over a guidewire into a vessel for removing plaque, and further showing the rotational direction of the atherectomy tip and the direction of fluid flow.
Figure 16C:
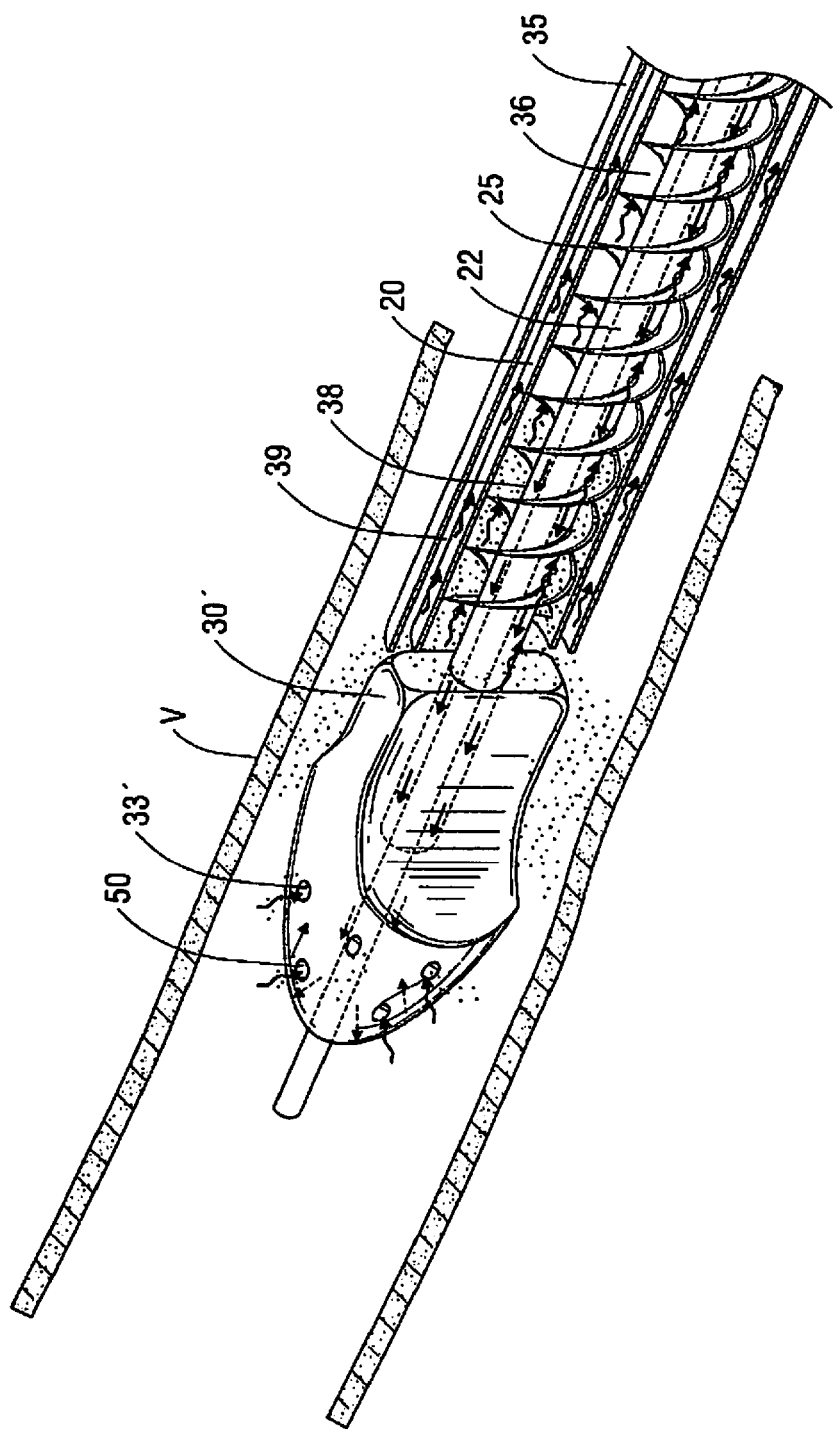
FIG. 16C is a view similar to FIG. 16B showing removal of the plaque from the vessel, the solid arrows illustrating fluid flow and the squiggly arrows illustrating the backflow of the particles (deposits)

Use of the atherectomy tip of the present invention is illustrated in FIGS. 16A-16C. As shown in FIG. 16A, plaque "P" buildup on the interior wall of the vessel "V" has occluded the passageway through the vessel. Tip 30' (or tip 30) is inserted over guidewire G and motorized rotation of flexible rotatable shaft 22 rotates the shaft 22 and attached rotatable tip 30' (or 30) at high speed in the direction of the arrow in FIG. 16B to remove plaque which comes into contact with its outer surface. High pressure fluid is injected in the direction of the solid arrow in gap 38 between the guidewire G and inner wall of inner shaft 22 to bounce off the internal distal wall of the tip 30' (or 30) and provide a rearward force to particles (deposits) received in the tip. Aspiration is provided to aspirate the broken off particles through openings 33' and 50 in the tip and through the gap 39 between the outer wall of the catheter 10 and the inner wall of the introducer sheath 35. The fluid flow is designated by the solid arrows and the aspiration is designated by the squiggly arrows in FIG. 16C. Thus, the cut plaque and debris can be removed from the patient's body as the particles are dislodged by the rotating tip 30' (or 30).

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical atherectomy apparatus for removing deposits such as plaque from an interior of a vessel, comprising:
   an outer member;
   a rotatable shaft positioned for rotational movement within the outer member by a motor, the rotatable shaft having a lumen extending therethrough dimensioned to receive a guidewire and a distal opening communicating with the lumen, the lumen having a cross-sectional dimension to enable fluid injection between an inner diameter of the rotatable shaft and an outer diameter of the guidewire; and
   a tip having a longitudinal axis and mounted to the rotatable shaft for rotation about its longitudinal axis upon rotation of the rotatable shaft, the tip having a distal internal surface at a distal end, the tip mounted to a distal portion of the rotatable shaft such that the distal opening of the rotatable shaft is axially spaced from the distal internal surface of the tip such that fluid injected through the lumen of the rotatable shaft contacts the distal internal surface of the tip and is redirected proximally through the tip from the distal end to a proximal end to direct in a proximal direction deposits removed by the rotational movement of the tip, the tip including a guidewire lumen for receiving the guidewire to enable over the wire insertion of the apparatus.

2. The surgical apparatus of claim 1, wherein the fluid is redirected proximally within the tip.

3. The surgical apparatus of claim 2, wherein fluid directed proximally within the tip exits proximally of the tip and into a gap between an outer diameter of the rotatable shaft and an inner diameter of the outer member.

4. The surgical apparatus of claim 3, wherein the tip has a plurality of side openings for aspiration of deposits.

5. The surgical apparatus of claim 1, wherein the rotatable shaft has an external threaded region to direct deposits proximally as the rotatable shaft is rotated.

6. The surgical apparatus of claim 5, wherein the deposits are aspirated between the rotatable shaft and the outer member.

7. The surgical apparatus of claim 1, wherein the deposits are aspirated proximally in a gap between an outer diameter of the rotating shaft and an inner diameter of the outer member.

8. The surgical apparatus of claim 7, wherein the deposits are aspirated external of the outer member.

9. The surgical apparatus of claim 1, wherein the atherectomy apparatus is insertable through an introducer sheath to access a target vessel containing the deposits.

10. The surgical apparatus of claim 9, wherein the introducer sheath has a side arm connectable to a source of suction so that deposits can be aspirated in the gap between the outer member and an inner diameter of the introducer sheath.

11. The surgical apparatus of claim 1, wherein the tip has an intermediate portion between distal and proximal portions, and a scalloped portion at the intermediate portion.

12. The surgical apparatus of claim 1, wherein a proximal end of the tip is spaced axially distally from a distal edge of the outer member.

13. The surgical apparatus of claim 1, wherein the fluid is redirected proximally external of the rotating shaft and provides a rearward force.

14. The surgical apparatus of claim 1, wherein the deposits are aspirated external of the outer member.

15. The surgical apparatus of claim 1, wherein the tip has a plurality of side openings for aspiration of deposits.

16. The surgical apparatus of claim 1, wherein a distal portion of the rotatable tip has a bullet shaped nose.

17. The surgical apparatus of claim 1, further comprising a plurality of longitudinally extending grooves formed in an outer surface of the tip to form an ablation surface.

18. The surgical apparatus of claim 1, wherein a distal region of the tip has a smaller transverse cross-sectional dimension than a proximal region of the tip.

* * * * *